United States Patent [19]
Jones

[11] Patent Number: 5,386,817
[45] Date of Patent: * Feb. 7, 1995

[54] ENDOSCOPE SHEATH AND VALVE SYSTEM

[75] Inventor: Jeffrey S. Jones, Salem, Va.

[73] Assignee: EndoMedical Technologies, Inc., Roanoke, Va.

[*] Notice: The portion of the term of this patent subsequent to Apr. 13, 2010 has been disclaimed.

[21] Appl. No.: 42,985

[22] Filed: Apr. 5, 1993

Related U.S. Application Data

[63] Continuation-in-part of Ser. No. 713,178, Jun. 10, 1991, Pat. No. 5,201,908.

[51] Int. Cl.⁶ .............................................. A61B 1/00
[52] U.S. Cl. ........................................ 128/4; 136/108
[58] Field of Search .............. 128/4, 6; 359/507, 510, 359/601, 611, 613, 642, 656

[56] References Cited

U.S. PATENT DOCUMENTS

| | | |
|---|---|---|
| 4,436,087 | 3/1984 | Ouchi ............................... 128/6 |
| 4,646,722 | 3/1987 | Silverstein . |
| 4,721,097 | 1/1988 | D'Amelio . |
| 4,741,326 | 5/1988 | Sidall et al. . |
| 4,779,611 | 10/1988 | Grooters et al. . |
| 4,809,678 | 3/1989 | Klein . |
| 4,825,850 | 5/1989 | Opie et al. . |
| 4,852,551 | 8/1989 | Opie et al. . |
| 4,869,238 | 9/1989 | Opie et al. . |
| 4,886,049 | 12/1989 | Darras . |
| 4,991,565 | 2/1991 | Takahashi . |
| 5,154,164 | 10/1992 | Chikama .............................. 128/4 |
| 5,201,908 | 4/1993 | Jones ................................... 128/4 |
| 5,274,500 | 12/1993 | Dunn ............................. 359/510 X |

FOREIGN PATENT DOCUMENTS

| | | |
|---|---|---|
| 3508833 | 9/1986 | Germany . |
| 3727003 | 2/1988 | Germany .............................. 128/4 |

Primary Examiner—Richard J. Apley
Assistant Examiner—Beverly A. Meindl
Attorney, Agent, or Firm—Ross & Stevens

[57] ABSTRACT

A protective covering for a medical instrument, such as an endoscope, is described. The covering includes an elongated hollow sheath having a wall of flexible material. The sheath is substantially gas and water impervious. The sheath further includes auxiliary access tubes associated with the sheath for providing a variety of functions, such as instrument manipulation, and fluid removal. The distal end of the sheath is provided with a cap having an optically clear window to allow the lens portion of the medical instrument to operate.

39 Claims, 11 Drawing Sheets

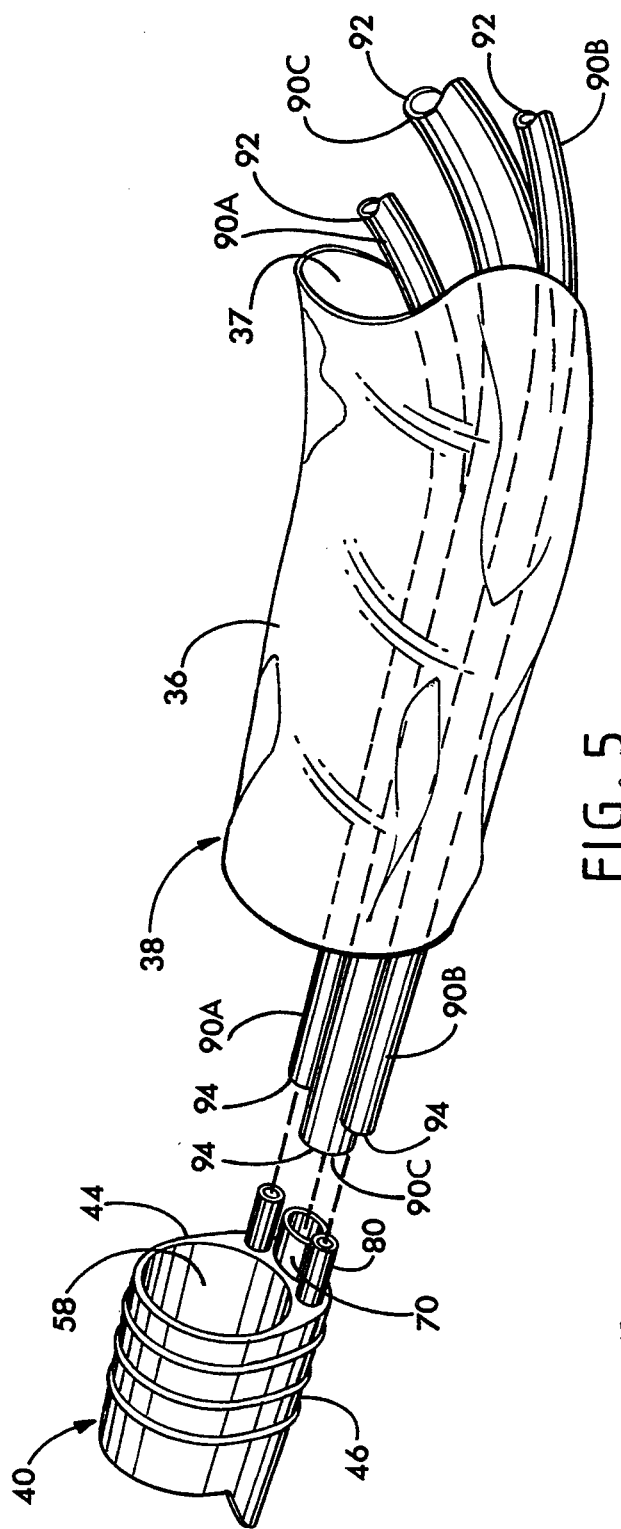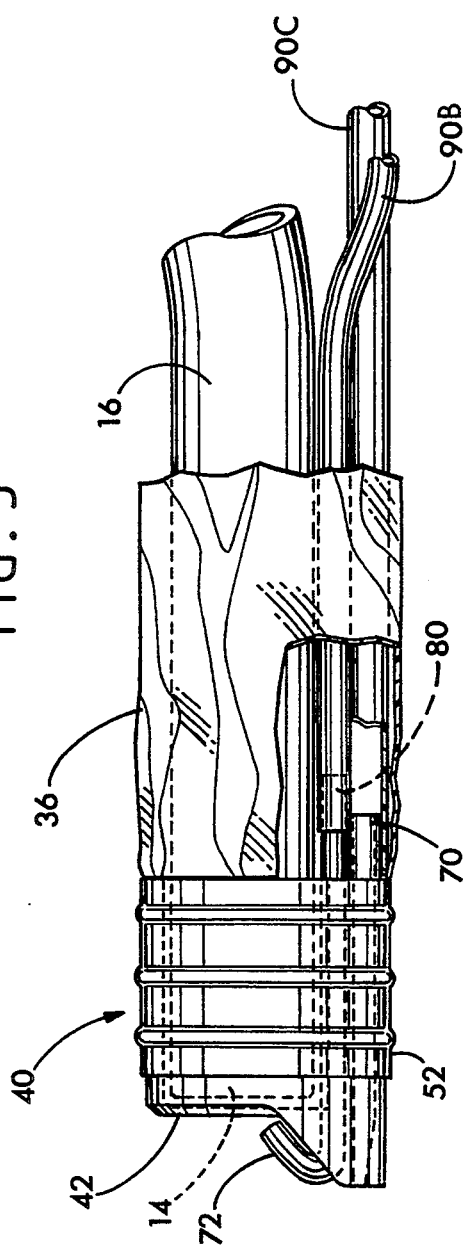

ENDOSCOPE SHEATH AND VALVE SYSTEM

REFERENCE TO RELATED INVENTION

The present invention is a continuation-in-part of U.S. patent application Ser. No. 07/713,178, filed Jun. 10, 1991 now U.S. Pat. No. 5,201,908, entitled "Sheath For Protecting Endoscope From Contamination," in the name of Jeffrey S. Jones, and incorporates this disclosure herein.

FIELD OF THE INVENTION

The present invention is directed to medical instruments and more particularly to conventional endoscopes. The present invention is specifically directed to a sanitary disposable protective covering for an endoscope, which covering shields the endoscope from the patient's body and from germs and other disease-bearing organisms. The present invention is also directed to a device for enhancing the functions of an endoscope, such functions including the provision of services including suction, biopsy, air and water.

DESCRIPTION OF THE PRIOR ART

It is an axiom of medicine that medical instruments invading or associating with a patient's body be extremely clean, if not sterilized. This is particularly true with instruments, such as endoscopes, which pass through a body orifice, such as the urethra, anus, etc. For purposes of the present invention, the term "endoscope" is intended to refer to a conventional endoscope, which includes an elongated substantially cylindrical portion, which portion is designed to enter a body cavity for examination and surgical purposes. All conventional endoscopes currently used in the market today include an elongated substantially cylindrical portion. One reason for this is to allow the distal end of the elongated portion to freely articulate. Any shape other than a substantially cylindrical shape would hinder the required flexibility of the distal end.

Unless these instruments are sterilized between use, the opportunities for passing disease-bearing organisms between patients is enhanced. Sterilizing medical instruments generally requires gas-sterilization. The process usually takes twenty-four hours and, as such, is not practical for instruments used several times a day. As a result, many instruments are soaked in a germicidal solution that is of questionable efficacy. The soaking takes at least ten minutes, which is advantageous over the gas sterilization process. However, the germicidal solutions tend to be caustic and will cause the premature destruction of the medical instruments.

Several alternatives are contemplated to resolve this problem. The use of disposable instruments, such as disposable endoscopes, has been suggested. However, this would result in an absurd cost, which is not justified. An alternative solution is the application of a sanitary disposable covering for the medical instruments. As an example, reference is made to D'Amelio U.S. Pat. No. 4,721,097, which discloses a disposable endoscope covering. The covering is provided with channels extending the length of the covering, which have the purpose of injecting air or gas into a patient's organs to provide better visibility or to allow the insertion of various mechanisms or devices in the body to perform manipulations.

Sidall et al. U.S. Pat. No. 4,741,326 is directed to a protective disposable covering for use with a medical instrument, such as an endoscope. The covering includes a transparent distal end plate. The end plate can be made of acrylic, glass or plastic material. The covering also includes a tube extending along the covering. The tube is adapted to accommodate a biopsy valve or other instrument. Additionally, the end plate has a nozzle means for directing air, water or other cleaning media onto the outer surface of the lens. However, this device allows the interior of the endoscope to become contaminated, which fundamentally differs from the present invention.

Klein U.S. Pat. No. 4,809,678 is directed to a disposable covering for an endoscope. The proximal end of the covering is elasticized to prevent seepage of liquids or other contaminants to the instrument. The distal end is transparent in order to allow the endoscope to function properly. Other references which disclose disposable coverings for endoscopes include Opie et al. U.S. Pat. Nos. 4,869,238 and 4,852,551.

SUMMARY OF THE INVENTION

It is an object of the invention to develop a disposable covering for a conventional endoscope that will prevent body fluids from contacting the scope while it is in use while preserving the visual capabilities of the scope and enhancing the scope's function.

It is also an object of the present invention to protect the patient from a contaminated scope.

It is further an object of the present invention to lessen the down time for cleaning and sterilization by providing a disposable sanitary protective covering for a medical instrument.

These objects and others are addressed by the present invention which is a protective covering for a conventional endoscope. A conventional endoscope includes an elongated substantially cylindrical portion having a distal end and a proximal end, an optical element and a light source. The protective covering of the present invention comprises an elongated hollow sheath having a wall of flexible material. The material is substantially gas and water impervious. The sheath includes a main channel for the elongated portion of the endoscope, a proximal end and a distal end. The distal end of the sheath comprises an end-fitting cap having a first end, a second end, a sidewall, and at least one access channel. The first end includes an optically clear element having an external surface and internal surface. The second end of the cap is in sealing engagement with the distal end of the sheath. The cover further comprises at least one axially-directed access tube. The access tube extends alongside and exterior to the elongated substantially cylindrical portion of the endoscope. The access tube has a distal and a proximal end. The access tube is separate from the sheath and tangentially located between the elongated substantially cylindrical portion of the endoscope and the wall of the sheath such that the access tube moves freely over the substantially cylindrical portion of the endoscope.

The protective covering prevents any contaminant material from touching any part of the interior or exterior of the endoscope. It is easily placed over the endoscope and provides enhanced biopsy, suction and lens-cleaning capabilities over just the scope itself. The covering provides air-water-suction-biopsy access tubes that fit between the endoscope and the sheath and bypass the internal channels provided by various scopes in the prior art. In this manner, the access tubes do not impede the viewing function of the endoscope.

An additional advantage of the present invention is that the diameter of the sheath is designed to be substantially larger than the diameter of the elongated portion of the endoscope. This allows the access tubes to move relatively freely in the space between the elongated portion of the endoscope and the sheath. Because of the relatively cylindrical shape of the access tube, the access tube will roll or move freely about the elongated portion of the endoscope as the elongated portion is manipulated. By moving freely between the sheath and the endoscope tube, the access tube will not restrict the movement of the endoscope tube in any way.

Further, the friction attachment at the distal end of the sheath inhibits the sheath from being displaced from the endoscope tube as the endoscope tube is being manipulated.

The protective covering of the present invention can also be made of relatively inexpensive materials. Thus, it is within the scope of the present invention to provide a disposable protective covering. Once the covering has been used, it can be discarded. However, the access channels in the endoscope do not need to be cleaned as they were not used. The conventional endoscope therefore remains free of contamination.

The end cap also allows for a watertight seal. Further, the present invention allows the lens of the endoscope to be placed adjacent the end plate of the end cap. In this manner, the lens of the endoscope retains its visual acuity, even when placed in the protective covering of the present invention.

The present invention is further directed to a combination protective covering and valve system for a conventional endoscope which includes an elongated substantially cylindrical portion having a distal end and a proximal end, an optical element and a light source. The system comprises an elongated hollow sheath as described above. The system further includes means to communicate a functional activity to the at least one access tube.

The present invention further includes a combination protective covering and valve system for a conventional endoscope as described above. The entire combination covering and valve system can be made of disposable materials. The system comprises an elongated hollow sheath having a wall of flexible material also as described above. The system further comprises a handle attachment adapted to be removably attached to the endoscope. The handle attachment comprises a manifold cover to detachably connect a valve system to the one access tube. The handle attachment further comprises at least one connector to detachably connect the valve system to the access tube.

Alternatively and preferably, the present invention comprises a combination covering and valve system in which the valve system includes remotely placed actuator buttons either removably placed on the endoscope body or placed elsewhere within the user's reach. The actuator buttons control the action of a remote valve system, which regulates the user of air, water, suction or another feature through access tubes directly connected to the valve system.

The valve system communicates with the access tubes of the protective covering in order to enable the endoscope user to perform the required task. Thus, the valve system and access channels in the sheath bypass the access channels normally in an endoscope, thereby eliminating the necessity of cleaning the endoscope. By using the valve and protective covering system of the present invention, it is also within the scope to be able to utilize an endoscope which does not have any access channels or valves.

Further objects, features and advantages of the invention will be apparent from the following detailed description when taken in conjunction with the accompanying drawings.

BRIEF DESCRIPTION OF THE DRAWINGS

In the drawings:

FIG. 3b is a cross-sectional view of an alternative embodiment of the end-fitting cap of FIG. 3a.

FIG. 5 is a partially exploded perspective view of the distal portion of the sheath of the present invention showing the attachment of the access tubes from the sheath to the end-fitting cap.

FIG. 6 is a partial cross-section side plan view of the distal portion of the sheath of the present invention showing the sheath attached to the end-fitting cap.

DETAILED DESCRIPTION OF THE INVENTION

The present invention is directed to any medical instrument having an elongated tubular portion. Specifically, the present invention applies to a variety of endoscopes for examining the body. Such examples include cytoscopes, upper endoscopes for the examination of the esophagus, stomach and duodenum, colonoscopes for examining the colon, angioscopes for examining blood vessels, bronchoscopes for examining the bronchi, laparoscopes for examining the peritoneal cavity, and arthroscopes for examining joint spaces. The present invention is advantageous in that it can be applied to a conventional endoscope having a substantially cylindrical or tubular portion. Depending upon the use of the endoscope, the endoscope tubular portion can vary in length from approximately 1-2 feet, and is designed to enter a body cavity for examination and surgical purposes. Controls at the proximal end, i.e., the manipulating end away from the patient, allow the distal end, i.e., the end entering the patient, to articulate in a variety of directions.

Figure 1:
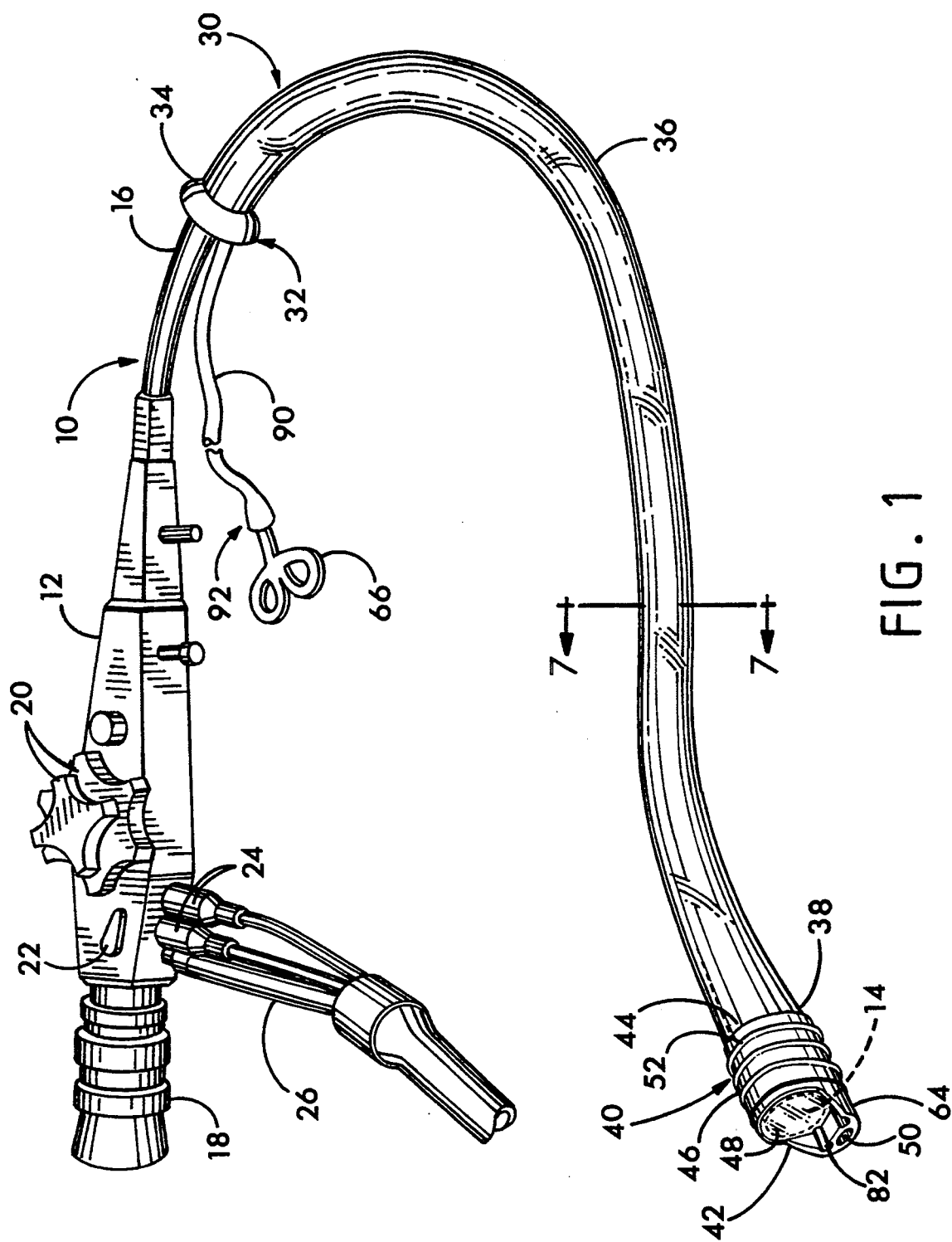
FIG. 1 is a plan view of a disposable protective covering for shielding an endoscope.

Referring now to the drawings, FIG. 1 illustrates an endoscope, which includes a conventional, flexible, basic endoscope, generally designated 10, and commonly used in the medical field. The endoscope includes an operating end or endoscope body portion 12 which permits, by manipulation of the user, i.e., the physician, a variety of operations to be performed. The endoscope also includes a distal end 14, illustrated in phantom. The operating end 12 and the distal end 14 are joined by a substantially cylindrical elongated flexible portion 16.

The operating end 12 generally includes an eye piece assembly 18, one or more control knobs 20, an inlet opening 22 through which an instrument such as a forceps is inserted, and air and/or water feed control devices 24, a suction control (not illustrated) and a light inlet means 26. The construction of the endoscope 10 is well-known to the art and does not form a part of this invention. Reference is made to Klein U.S. Pat. No. 4,809,678, Opie et al. U.S. Pat. No. 4,825,850, and Opie et al. U.S. Pat. No. 4,852,551 for a variety of descriptions of endoscopes.

According to the present invention, a relatively loose-fitting, flexible, protective covering 30 is provided to protect the flexible portion 16 of the endoscope 10 from contamination. Substantially all of the flexible portion 16 of the endoscope 10 will be covered.

The covering 30 comprises a sheath 36 characterized by being flexible, loose fitting over the elongated portion 16 of the endoscope 10, and substantially gas and water impervious to prevent the invasion of contaminants to and from the endoscope 10. The sheath material can be elastomeric and include polymeric resinous materials such as natural and synthetic rubbers, thermal plastic polymeric materials such as polyethylene, polypropylene, polyurethane and combinations of natural or synthetic rubbers with thermal plastic polymeric materials such as rubber-modified polyethylene, rubber-modified polystyrene and the like.

The proximal end 32 of the sheath 36 may be sealingly engaged to the flexible portion 16 of the endoscope 10 by means of a constriction band 34 or the like. The constriction band 34 forms a friction attachment between the sheath 36 and the flexible portion 16 and inhibits the sheath 36 from slipping down the flexible portion 16 toward the distal end 14 of the endoscope 10. The constriction band can be made from a variety of materials known to the art and can be in the form of a metal or plastic clip, rubber band, friction tape or the like.

Figure 3A:
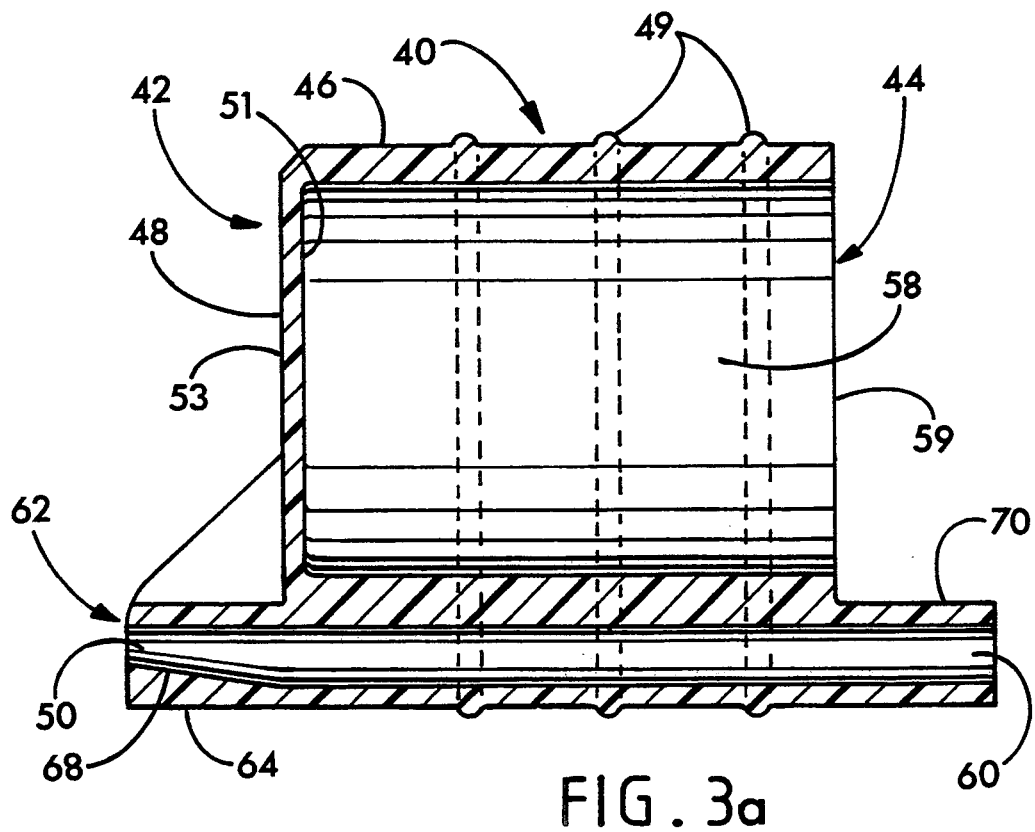
FIG. 3a is a cross-sectional view of the end-fitting cap of FIG. 2 taken along lines 3—3 of FIG. 2.

Located opposite to the proximal end 32 of the sheath 36 is the distal end 38. The distal end 38 includes an end-fitting cap (endcap) 40 having a first distal end 42, a second proximal end 44, and a generally cylindrical wall 46. The first end 42 includes an optically clear element or window 48 of optically clear glass or plastic to serve as a window for the endoscope optics located at the distal end 14 of the flexible portion 16 of the endoscope 10. The window has an internal surface 51 and an external surface 53 as illustrated in FIG. 3a. In this manner the protective covering 30, comprising both the sheath 36 and the endcap 40, serves as a protection against contamination while still allowing the endoscope 10 to perform the required task of viewing.

The endcap 40, including the window 42, can be made of a number of materials known to the art. The endcap 40 is preferably constructed of flexible, semi-rigid or rigid plastic or rubber material, to form some structural integrity over the end of the endoscope 10. Preferred examples of materials include styrene, plexiglass and polyvinyl chloride. It is also within the scope of the present invention to provide a window 48 with magnifying capabilities.

It is within the scope of the present invention to provide the window 48 at the first end 42 or along the side wall 46 as required by the purpose of the endoscope. As such, some endoscopes are constructed such that the optical element is a side-viewing optical element.

The endcap 40 is provided with a utility opening 50 which extends from the first end 42 of the endcap. This opening 50 will be described in more detail later in the specification.

The second end 44 of the endcap 40 can be sealingly engaged at the distal end 38 of the sheath 36 by a connector 52, which is described in my prior disclosure referred above in the Reference to Related Invention, or it may be sealingly engaged with the distal end 38 of the sheath 36 by connectors 52, known to the art, such as glue, tape or other sealants. One connector 52, in the form of friction or sealing tape, is illustrated in FIG. 6.

Figure 2:
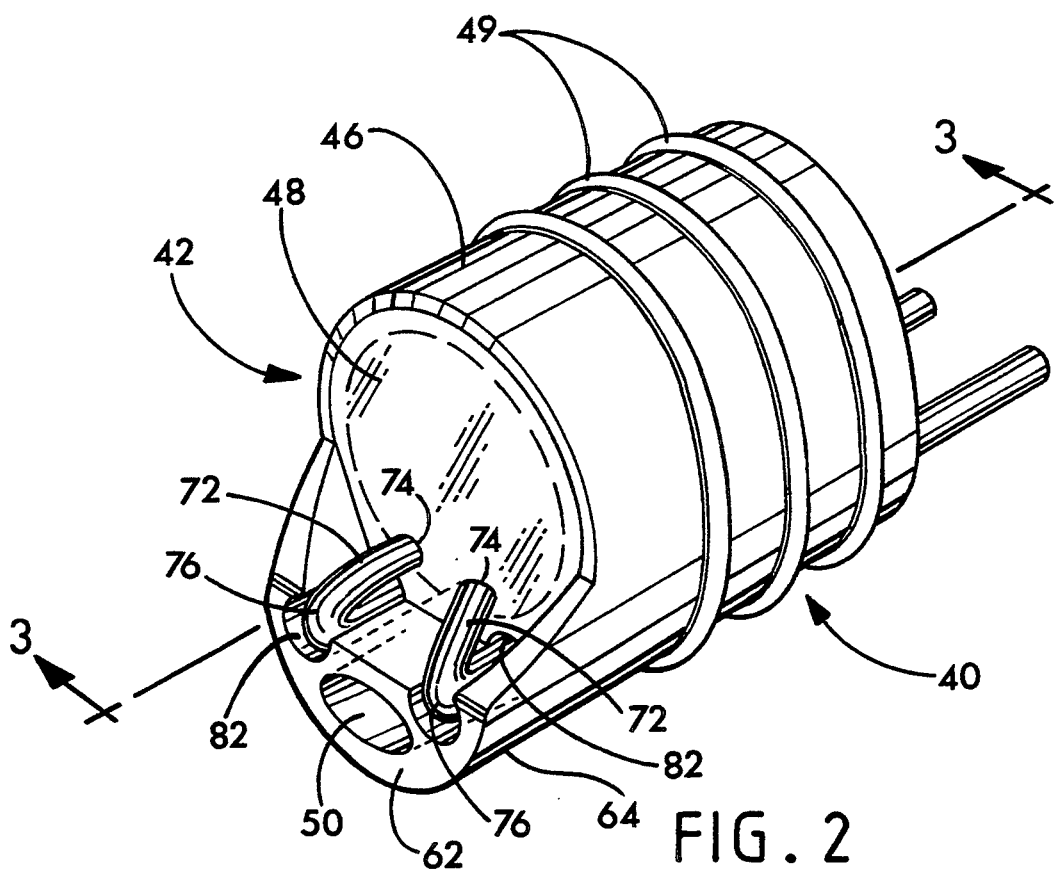
FIG. 2 is an enlarged perspective view of an end-fitting cap of the endoscope covering at the distal portion of the endoscope.
Figure 3B:
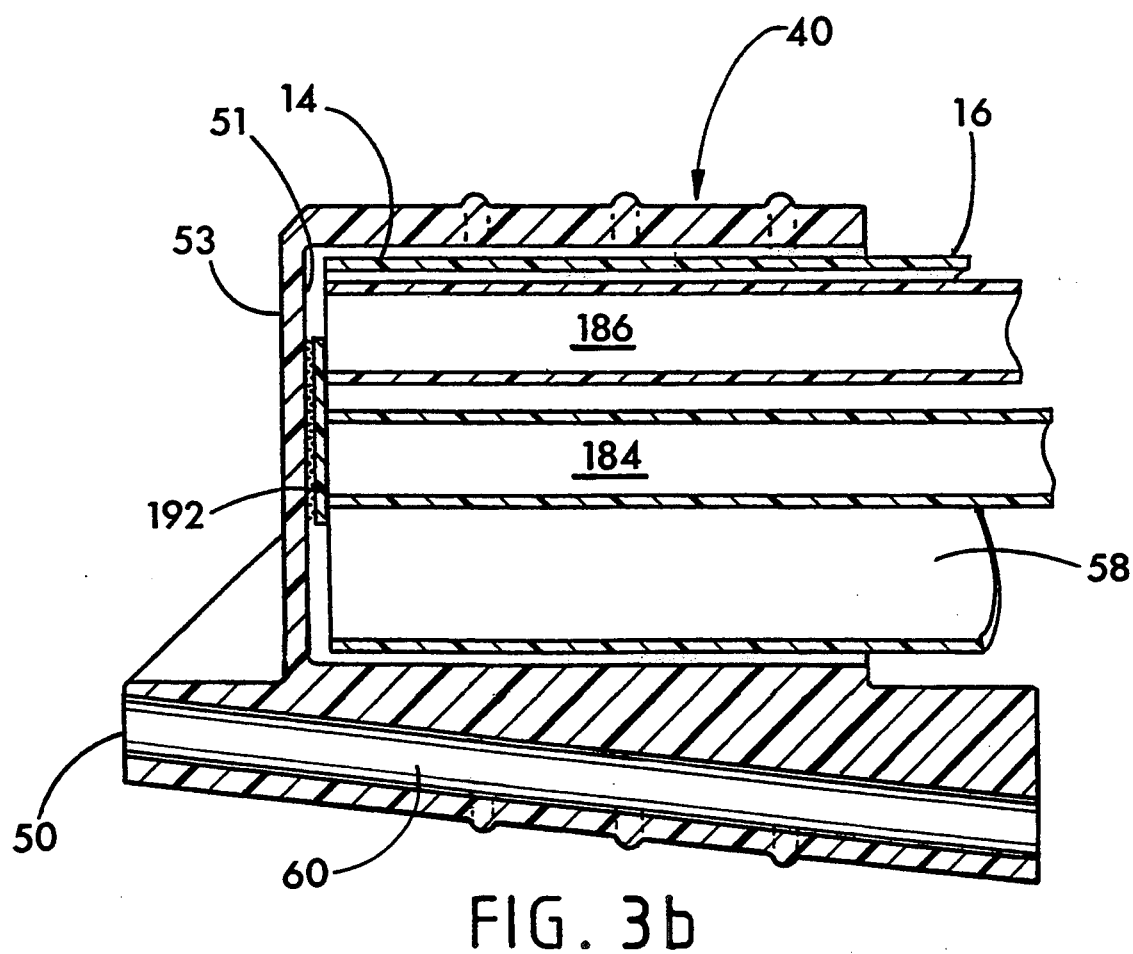
Figure 4:
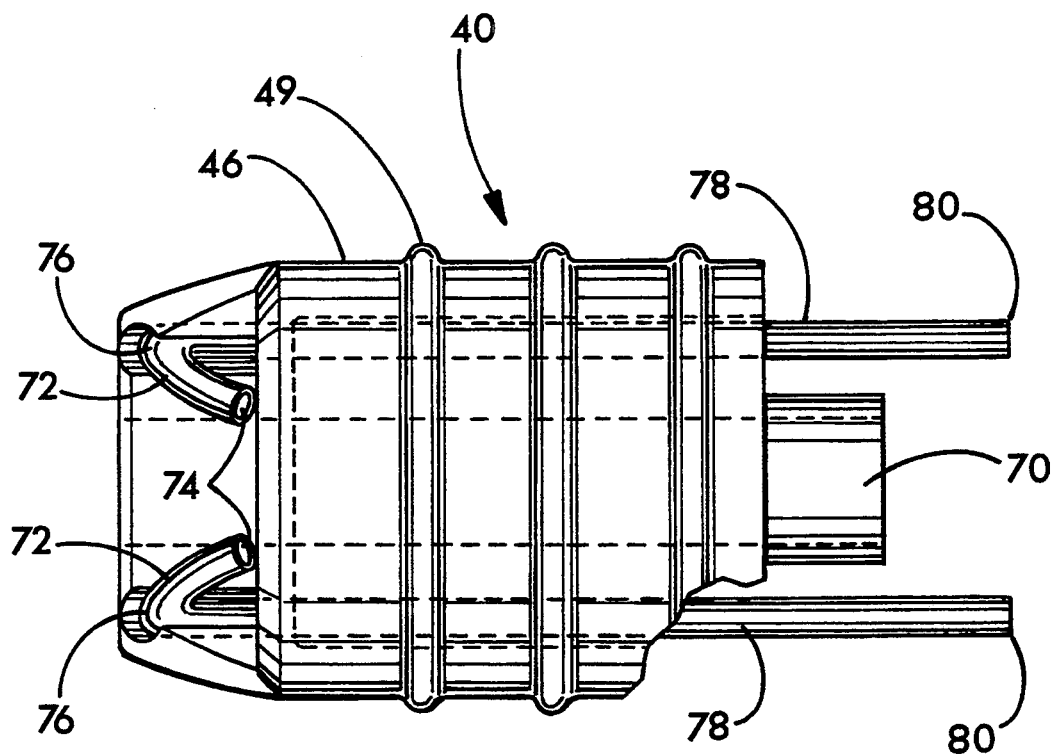
FIG. 4 is a partial cross-sectional top plan view of the end-fitting cap of FIG. 2.

Reference is now made to FIGS. 2-4 for a detailed description of a preferred embodiment of the endcap 40 of the present invention. As described previously, the endcap 40 is formed with a substantially cylindrical sidewall 46 open at the proximal end 44 of the endcap 40 to receive the distal end 14 of the flexible portion of the endoscope 10. The distal end 42 of the endcap 40 is bordered by the endcap window 48.

The sidewalls 46 of the endcap 40 are preferably provided with circumferential ridges 49 to insure a tight friction fitting between the sheath 36, the endcap 40 and the connector 52. The endcap 40 is provided with an endoscope chamber 58, which receives the distal end 14 of the flexible portion 16 of the endoscope 10 as illustrated in FIG. 6.

The endcap 40 is also provided with an access channel 60, a tubular channel extending along the sidewall 46 substantially parallel to the endoscope chamber 58, as illustrated in FIG. 3a. The distal end 62 of the access channel 60 is peripherally located on the first end 42 of the endcap 40 and includes an extension 64 beyond the first end 42 to an opening 50. The extension 64 provides a number of advantages. First, the extension 64 provides a location for providing a spray port 72 to provide spray cleaning access to the exterior of the window 48. Second, the extension opening 50 provides a manipulating feature for the instrument 66. The extension 64 extends a sufficient distance from the distal end 42 of the endcap to allow the user to observe a surgical tool or instrument, illustrated in FIG. 1 at 66, when the instrument initially exits from the opening 50 of the access channel 60. This extension is important as it will allow the user to accurately manipulate the instrument 66 and protect the patient's body tissue from damage. The extension 64 enables the surgeon to determine exactly when the surgical tool 66 exits the endcap 40. Without this determination the surgeon may have a blind spot, which requires the surgeon to extend the surgical tool 66 from the endcap 40 a substantial distance from the opening 50 before the surgeon is able to see the surgical tool. Without being able to observe the instrument initially extending from the endcap 40, it is possible for the instrument to puncture patient tissue such as a bowel wall before the surgeon can see the instrument.

Referring to FIG. 3a, the access channel 60 is preferably provided with a ramp 68, which angles upwardly toward the opening 50 of the endcap access channel 60. The ramp 68 allows the exiting instrument 66 to angle upwardly toward the middle of the window 48 and away from the body cavity wall being inspected. This is a safety feature. It is within the scope of the present invention to provide the ramp 68 with an articulation feature so that the instrument 66 can actually be moved as it was being pushed through the exit. This could be done with a mechanical actuator or a tiny balloon device under the ramp 68 that can be inflated or deflated with air or water and controlled from the operating end 12 of the endoscope 10.

FIG. 3b illustrates an alternative embodiment to the ramp 68 of FIG. 3a. Rather than using an angled ramp 68, the entire endcap 40 may be machined such that the endcap access channel 60 is angled toward the center of vision of the window 48.

The proximal end 44 of the endcap 40 extends beyond the opening 59 of the endoscope chamber 58 to provide an endcap access channel connection end 70.

Referring now to FIGS. 2 and 4, there is also illustrated a window washing system for clearing the window 48. The system comprises at least one and preferably two washer ports 72 having an exit end 74 opening to the window. The ports 72 are characterized by bends 76 leading to a straight section 78 which ends at a second access channel connection end 80. The ports 72 pass through access channels 82 in the endcap 40 on either side of the access channel 60. Unlike most prior art washer ports, in which the spray washer fluid sprays tangentially onto the window 48, the ports 72 of the present invention preferably spray the fluid onto the window 48 at a 70°–90° angle to provide better cleansing action.

Referring now to FIG. 5, the sheath 36 is provided with at least one and preferably more axially directed access tubes 90 extending in axial fashion along inner wall 37 of the sheath 36 from the operating end 12 of the endoscope 10 to the endcap 40. The sheath 36 may be provided with one access tube 90 as shown in FIG. 1, or several tubes 90A, 90B, 90C as shown in FIGS. 5 and 6.

The access tubes 90 have a proximal end 92 and a distal end 94, associated with the distal end 38 of the sheath 36. As shown in FIGS. 5 and 6, the access tubes 90 are separate tubular channels extending axially between the elongated flexible portion 16 of the endoscope 10 and the inner wall 37 of the sheath 36.

The proximal end 92 of the access tubes 90 may be attached or otherwise associated with the endoscope body 10 for ease of use by the surgeon. Otherwise, it can be loose, i.e., not attached to the endoscope as illustrated in FIG. 1. One purpose of the access tubes 90 is to allow passage of a biopsy tool or instrument 66 through the tube 90 to the distal end 62 of the access channel 60 in the endcap 40. In this manner the instrument 66 can be manipulated by a surgeon to perform a surgical task such as a biopsy.

FIGS. 5–6 illustrate a preferred embodiment of the endcap 40 of the present invention, including at least three access tubes 90A, 90B, 90C and the endoscope chamber 58 to receive the flexible portion 16 of the endoscope 10. The access tubes 90 extend alongside the endoscope's flexible portion 16 rather than through the endoscope as in many prior art instruments. In this manner, the air/water/suction/biopsy tubes in a conventional endoscope are not used and therefore do not become contaminated, which avoids the necessity of cleaning and sterilizing the endoscope 10.

As illustrated in FIGS. 5–6, there are three access tubes 90A, 90B, 90C, each of which provide a required service. In this embodiment, access tubes 90A and 90B are attached to a pump element (not shown) for providing fluids to the patient's body. In the illustrated embodiment, one of the tubes 90A or 90B provides the fluid used to wash the window 48. The other tube is used to deliver fluid such as air to the viewing area. The tubes 90A and 90B are attached at the distal end 38 of the sheath 36 to the second access channel connection ends 80 of the window washer ports 72 to provide fluid flow through to the exit ends 74 of the ports 72. The cleaning fluid is pressurized by means of a pump system (not illustrated) in association with the endoscope 10.

Access tube 90C is generally provided for the dual purpose of manipulating the surgical instrument 66, illustrated in FIG. 1 and providing suction to withdraw fluid from the viewing area. The instrument 66 is manipulated by the surgeon via access means at the proximal end 92 of access tube 90C. The instrument may be in the form of a forceps, which is inserted into the body for medical treatment. The forceps is manipulated by the surgeon, who can see the end of the forceps via the window 48. The tube 90C is attached near the distal end 38 of the sheath 36 to the first access channel connection end 70.

Figure 7:
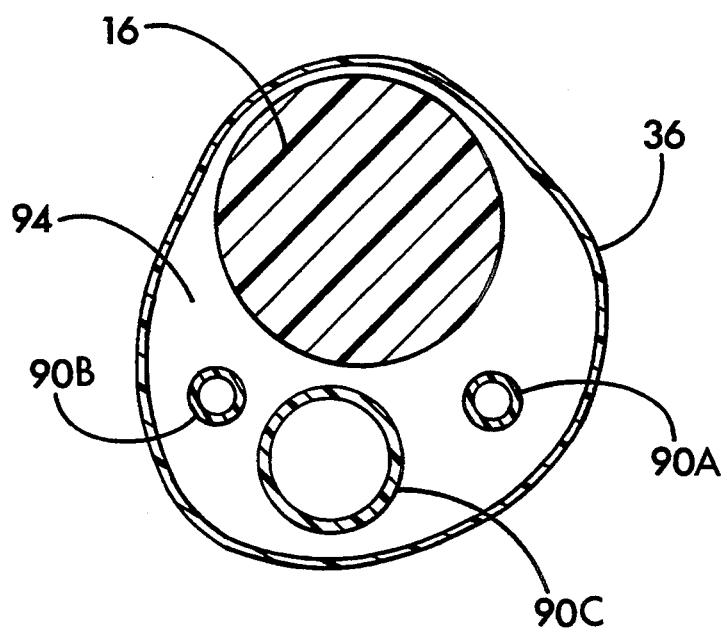
FIG. 7 is a cross-sectional view of the sheath taken along lines 7—7 of FIG. 1.

Reference is made to FIG. 7 for a cross section of sheath 36 with the interiorly placed elongated portion 16 of the endoscope 10 and the access tubes 90A, 90B and 90C. As illustrated in FIG. 7, it is intended that there will be sufficient free or air space 94 to allow the tubes 90 to move freely over the elongated portion 16 as the endoscope 10 articulates.

A method of using the protective covering 30 will now be described. In the embodiment illustrated in FIG. 1, the sheath 36 is applied to the flexible portion 16 of the endoscope 10 by sliding the flexible portion 16 of the endoscope 10 in the inner wall 37 of the sheath 36 and alongside the access tubes 90 until the distal end 14 of the flexible portion 16 of the endoscope 10 enters the endoscope chamber 58 of the endcap 40 and aligns next to the window 48. The proximal end 32 of the sheath 36 is then friction fit onto the flexible portion 16 of endoscope 10 at its proximal end by means of the connector 34.

It is also anticipated that the protective covering 30 may be provided in a rolled-up manner to be applied to the flexible portion 16 by unrolling the sheath 36. After the sheath 36 has been placed on the flexible portion 16 of endoscope 10, the endoscope is then used in a normal medical procedure known to those skilled in the art. Because the diameter of the sheath 36 is substantially large enough to accommodate both the flexible portion 16 of the endoscope 10 and the access tubes 90 and allow relatively free movement between the tubes 90 and the flexible portion 16 as the flexible portion 16 is articulating, the sheath 36 does not restrict the movement of the endoscope 10 during a surgical procedure.

After the medical procedure has been completed, the sheath 36 can be removed by peeling it away from the endoscope flexible portion 16. The entire covering 30 can then be disposed. It is also within the scope of the present invention to provide reusable coverings 30 which can be re-sterilized for subsequent use.

Figure 8:
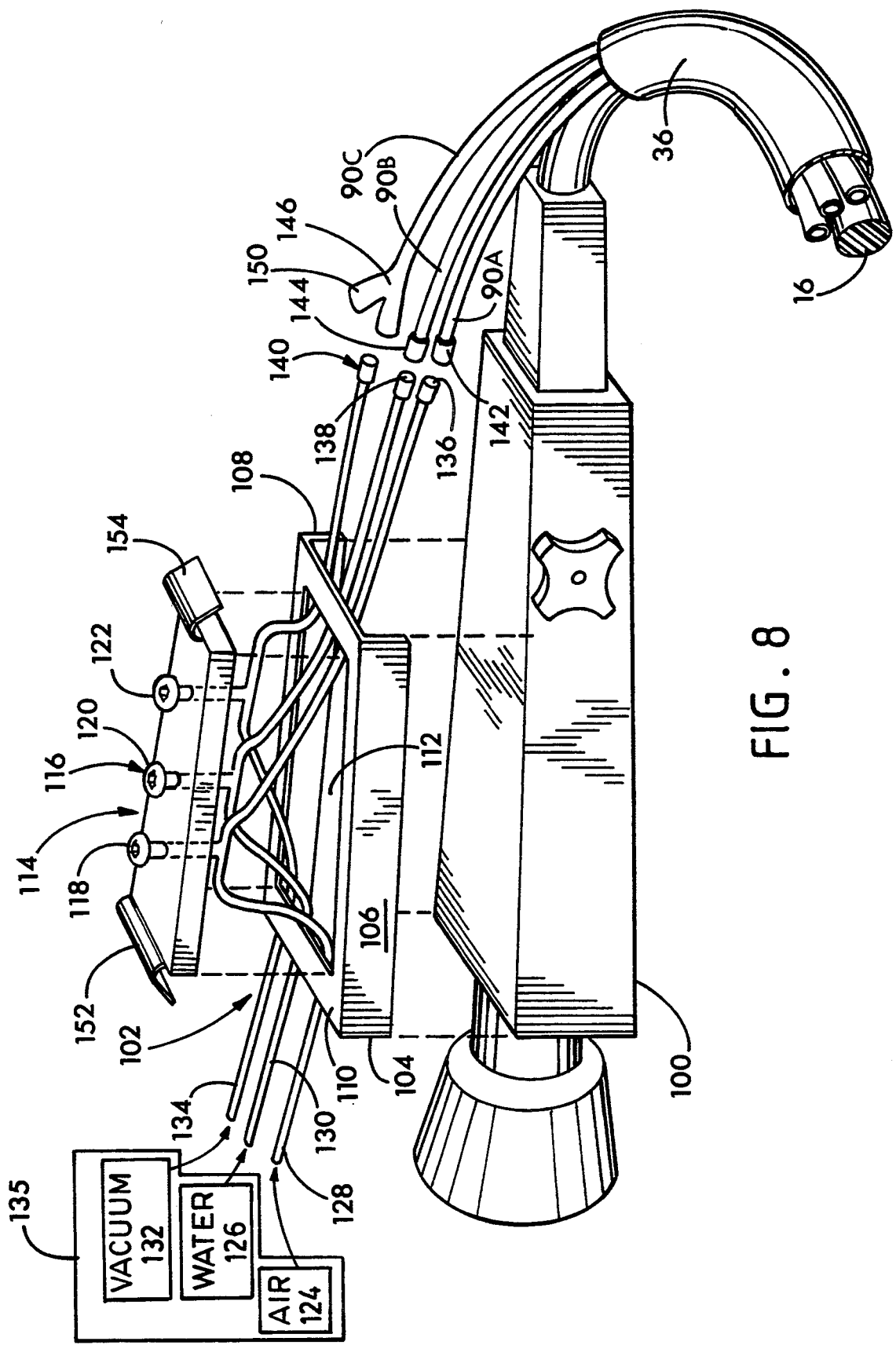
FIG. 8 is a partially exploded perspective view of another embodiment of the present invention illustrating the protective covering in combination with a valve system.
Figure 9:
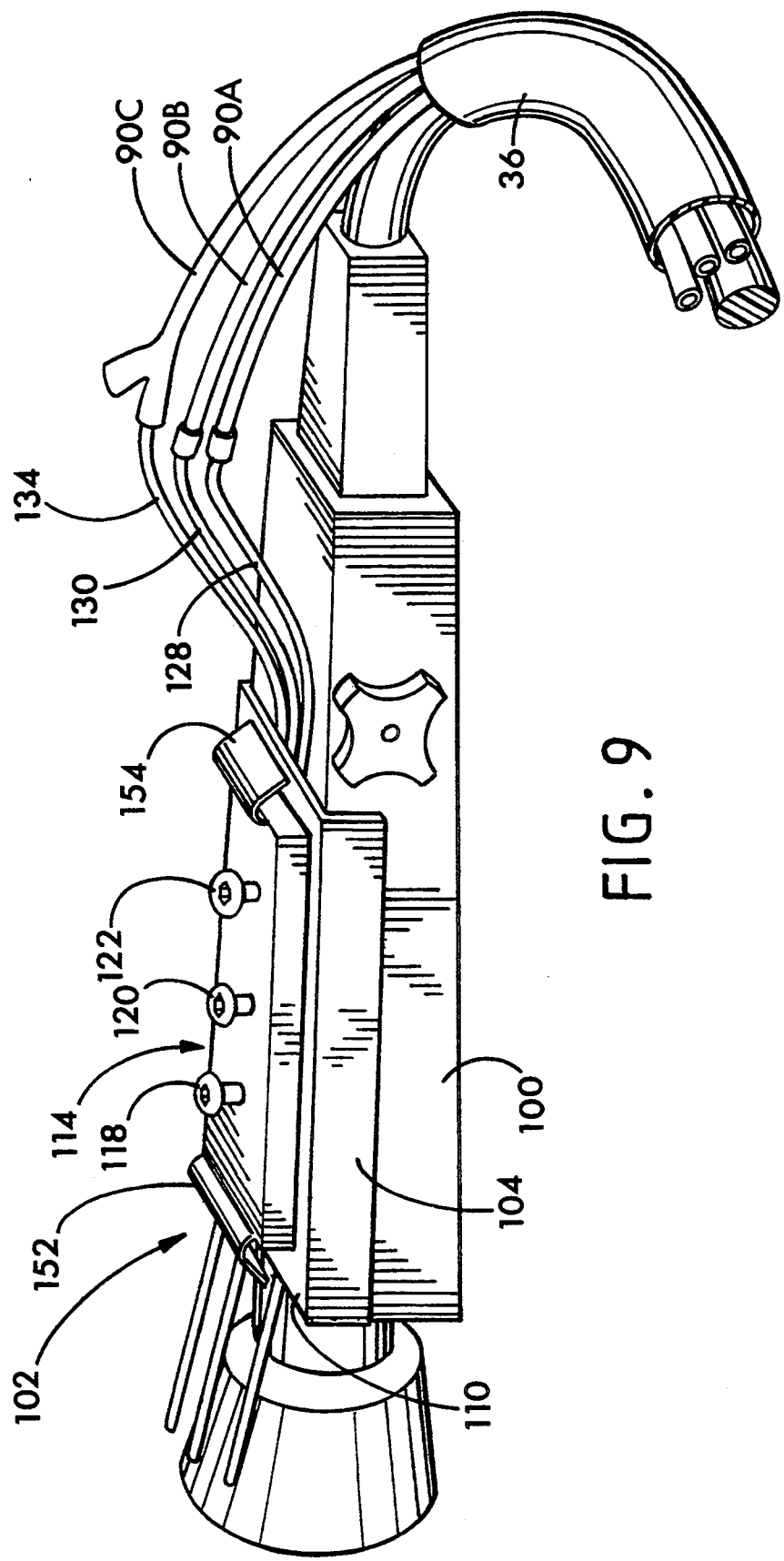
FIG. 9 is an intact perspective view of the embodiment of FIG. 8.

Reference is now made to FIGS. 8 and 9 for an alternative embodiment of the protective covering for the endoscope. These figures are directed to a detachable valve system for a conventional endoscope. The valve system is provided to communicate a functional activity to the access tubes. Examples of functional activity include but are not limited to supplying fluids such as air or water or an irrigating fluid known to the art, and suction or vacuum capabilities. The valve system includes a manifold cover for detachably connecting a valve or actuators for valves or other devices, collectively referred to as actuator buttons 116, to the endoscope body. The actuator buttons communicate with the access tube of a protective covering in order to enable the endoscope user to perform the required task. The valve system further includes connecting means to connect the manifold to the endoscope body, and connecting means to detachably connect the manifold to at least one access tube.

FIGS. 8 and 9 illustrate a standard endoscope 100, known to the art and described herein. Unlike the endoscope 10 described and illustrated in FIG. 1, the endoscope 100 does not require air and water feed control devices integrated with the scope. These features are provided by a removable manipulation handle, generally designated at 102. The handle 102 includes a manifold cover 104 designed to be secured, frictionally or otherwise, to the outer surface of the endoscope body. The manifold cover 104 includes securing side pieces 106, 108 and an upper surface 110 with an opening 112. The opening 112 is designed to receive a manifold 114 which includes the actuator buttons 116.

The actuator buttons 116 are a series of valves, which are manipulated by a surgeon to perform a series of tasks. As illustrated in FIGS. 8 and 9, there are three finger controls 118, 120, 122. It is within the scope of the invention to provide more or fewer valves depending on the endoscope used and the requirements of the operation. The action and operation of the actuator buttons 116 are well known to the art and, with the exception of the manner of placement on the endoscope 100, do not form part of this invention. Reference is made to Opie et al. U.S. Pat. Nos. 4,825,850, 4,852,551 and 4,869,238, which are incorporated herein for a description of valve systems in endoscopes.

As herein illustrated, finger controls 118 and 120 are designed to provide air and water, respectively, to the patient from an air source 124 and a water source 126 through air communicating channel 128 and water communicating channel 130. Valve 122 is a suction valve attached to a vacuum system 132 by means of suction channel 134.

The handle 102 in FIGS. 8 and 9 can be made of disposable materials. After use, the handle 102 and its access tubing can be discarded along with the sheath 36. In this embodiment, the handle 102 is attached to the endoscope 100 and the control lines 128, 130, 134 are connected to the air 124/water 126/vacuum 132 source, referred collectively as the power box 135. The only function of the power box 135 is to supply air, water and suction, which are controlled through the finger controls 118, 120, 122. This type of structure keeps the handle 102 very light and provides the handle 102 with few working parts thereby making it relatively inexpensive to make and therefore disposable. Because this mechanism does not touch the patient, it will also generally stay clean and consequently not need to be replaced often.

There is also contemplated a trap (not shown) between the suction tubing 134 and the vacuum valve 132 in the vacuum source so that the vacuum valve 132 remains clean. The air/water lines 128, 130 do not need a trap since the flow is from the source to the patient.

Figure 10:
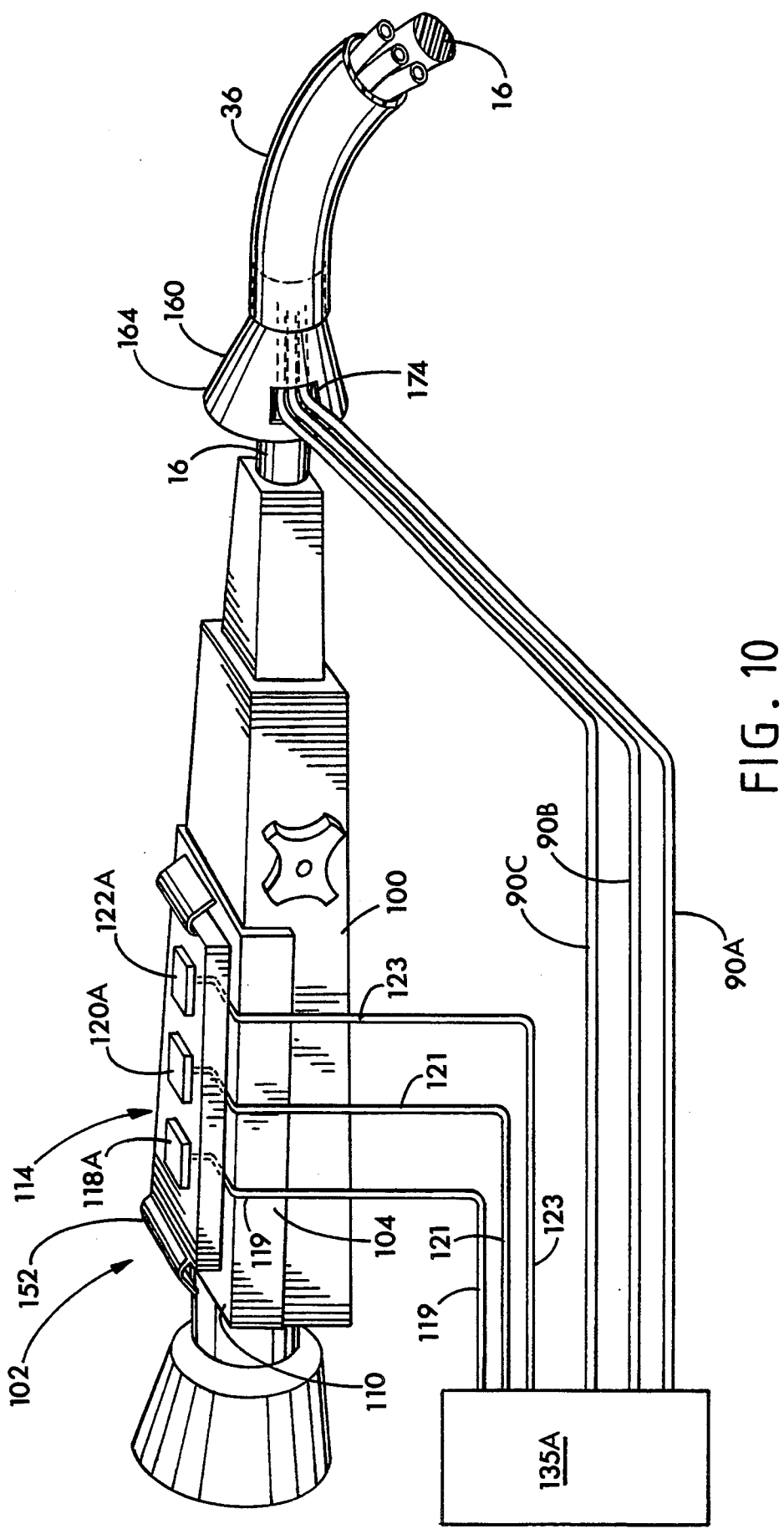
FIG. 10 is a partially exploded perspective view of another embodiment of the present invention illustrating the protective covering in combination with a valve system.
Figure 11:
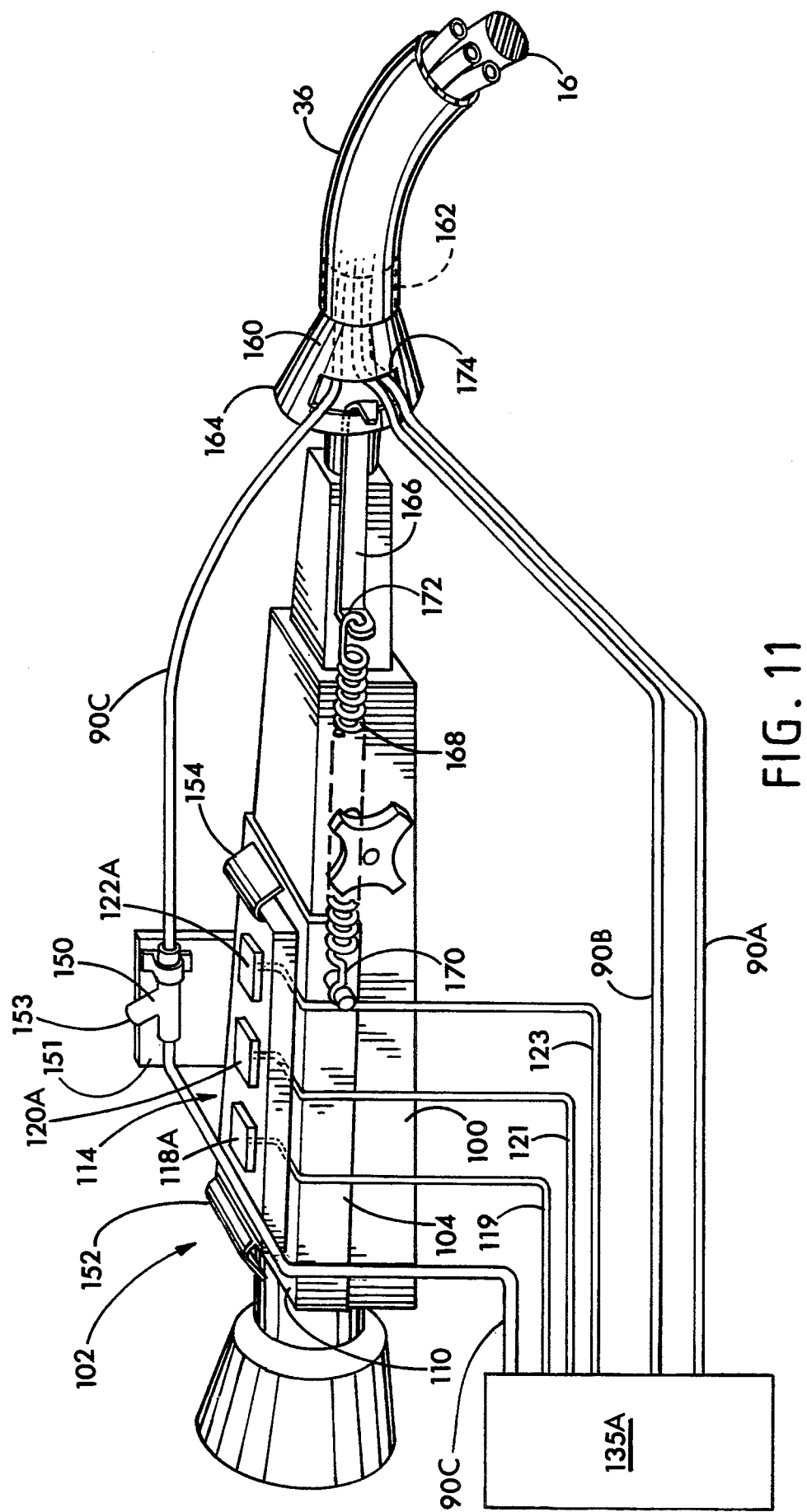
FIG. 11 is a side plan view of the embodiment of FIG. 8, illustrating an alternative method of connecting the endoscope sheath to the endoscope.

Reference is made to FIGS. 10 and 11 for an alternative valve system. In the embodiment, the present invention is provided with remote valves (in power box 135A) and actuators 118A, 120A, 122A on the handle 102, which can be driven with air, hydraulics, mechanically or electrically. In the embodiment illustrated in FIGS. 10 and 11, the finger controls 118A, 120A and 122A are spring-biased buttons. The buttons 118A, 120A and 122A are preferably electrically connected to the power box 135A by connection wires 119, 121 and 123 respectively. The buttons 118A, 120A and 122A therefore electronically control the appropriate valves (not illustrated) in the power box 135A. It is also within the scope of this embodiment to use pneumatic actuators in which case the wires 119, 121 and 123 would be tubes to conduct air.

The remotely placed electrically actuated valves in the power box 135A control the air, water and suction which may be directly connected to the appropriate access tubes 90A, 90B and 90C as illustrated in FIG. 10. In this manner, the air/water/suction tubing is completely separate and is therefore disposable. It is within the scope of the present invention to include other actuator buttons on as needed basis. For example, an actuator button could be provided to adjust the ramp 68 as illustrated in FIG. 3.

It is within the scope of the present invention to provide one of the access tubes, here: 90C, with a biopsy instrument access port 150. The biopsy instrument access port 150, illustrated herein as a "Y" connector. The biopsy instrument access port 150 may be attached to the handle 102 by means such as a bracket 151, as illustrated on FIG. 11, which keeps the access port 150 firmly in place making the biopsy easier. Therefore, access tube 90C serves the dual purpose of providing a vacuum if required or providing a channel through the secondary bracket opening 153 for a biopsy instrument.

The manifold 114 may be provided with winged tabs 152, 154 to assist the surgeon in manipulating the finger controls 118A, 120A, 122A in use. In operation, the surgeon may place the little finger and thumb of one hand under the tabs 152, 154 to assist in manipulating the endoscope 100. The remaining fingers will then be available to manipulate the finger controls 118, 120, 122 in much the same manner that one would play a horned instrument such as a trumpet.

Reference is now made to FIG. 11, which illustrates an alternative and preferred method of securing the endoscope sheath 36 to the endoscope 100 and the handle 102. This embodiment is equally applicable to the endoscope/sheath arrangement illustrated in FIG. 1. Rather than using a constriction band 34 at the proximal end 32 of the sheath 36 as illustrated in FIG. 1, the alternative embodiment utilizes a collar 160 having a substantially cylindrical neck portion 162, which is designed to be attached to the proximal end 32 of the sheath 36. The collar 160 also preferably has a flared mouth portion 164 for receiving the distal end 14 of the flexible portion 16 of the endoscope 100 as the flexible portion 16 is fed into the sheath 36.

The collar 160 is also provided with means to engage the sheath 36 to the endoscope 100. One form of the engagement means is illustrated as a fastener 166 such as a hook connected to either the endoscope 100 or the handle 102 as illustrated. The fastener 166 is preferably connected to the handle 102 by spring biasing means 168 connected at one end 170 to the handle 102 or the endoscope 100 and at the other end 172 to the fastener 166. The fastener 166 is designed to engage the collar 160 by means of a cut out portion or notch 174 in the mouth 164 of the collar 160. The fastener 166 engages the notch 174 thereby holding the sheath 36 in place so that the sheath 36 cannot loosen and work its way toward the distal end 14 of the flexible portion 16 of the endoscope 100. The fastener 166 also assists the reducing any slack in the sheath 36 so that the endcap 40 will be held tightly against the distal end 14 of the endoscope 100. The spring biasing means 168 provides constant tension on the sheath 36.

Figure 12:
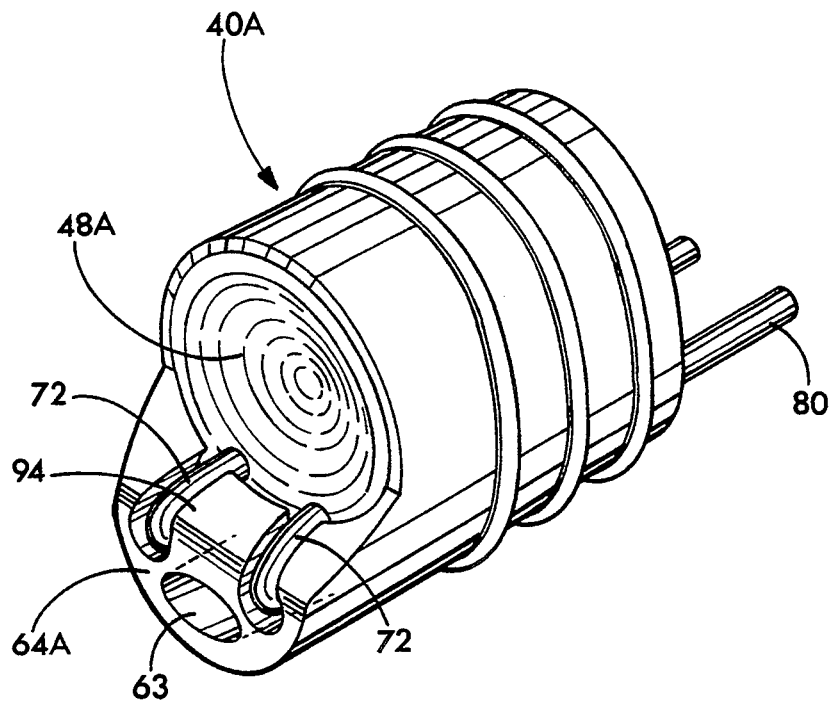
FIG. 12 is a perspective view of an alternative embodiment of the end-fitting cap of the present invention.

Reference is now made to FIG. 12 for an alternative embodiment of the end-fitting cap 40A of the present invention. The end-fitting cap differs from the end-fitting cap illustrated in FIGS. 1-4 in two basic ways. The window 48A has a concave curvature in the optical part. The concave curvature is not intended for magnification as much as it reduces glare from the light source in the distal end 14 of the endoscope 10. The concavity alters the angle of light reflection away from the operator. The result is a reduction in light glare flashing back in the operator's eyes.

The extension 64A in the end-fitting cap 40A also differs from the end-fitting cap 40 in FIGS. 1-4 in that the area 94 surrounding the ports 72 is built up around the ports to smooth the transition from the extension 64A to the body of the end-fitting cap 40A. Thus, the entire end-fitting cap 40A is more streamlined without any significant projections.

Figure 13:
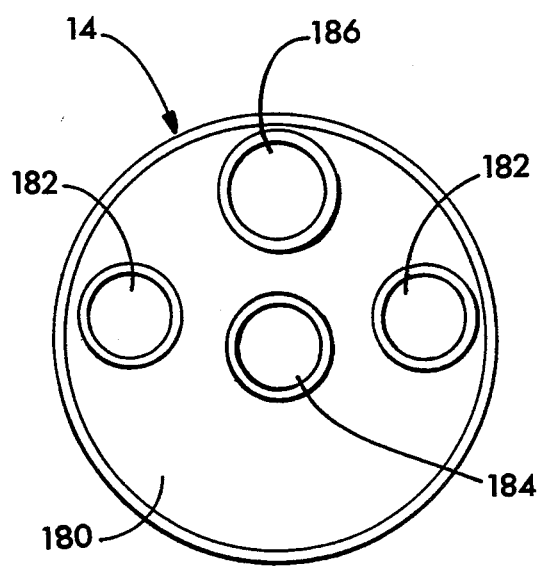
FIG. 13 is a front plan view of the distal end of a typical endoscope.
Figure 14:
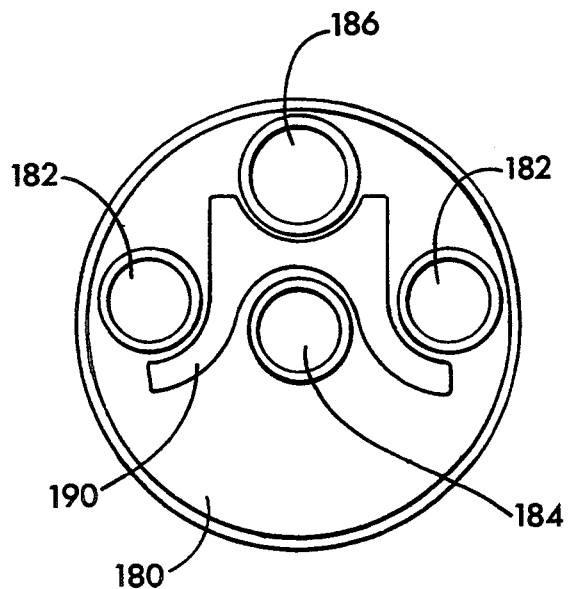
FIG. 14 is a front plan view of the distal end of the endoscope of FIG. 13 illustrating a shadow mask attached thereon.
Figure 15:
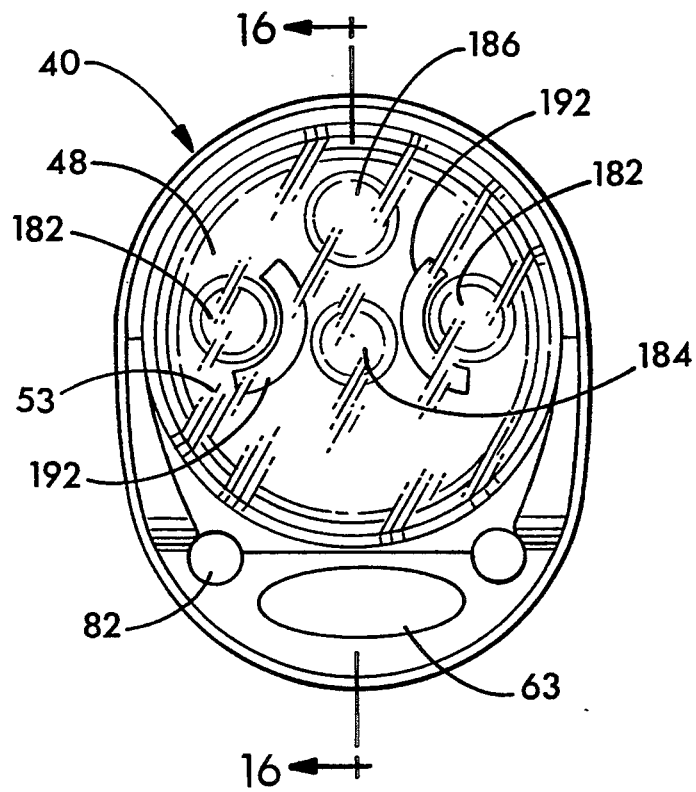
FIG. 15 is a front plan view of the distal end of the endoscope cap of the present invention illustrating an endcap shadow mask designed to be placed directly on the interior surface of the window of the endcap.

Another way to reduce the light glare flashing back into the operator's eyes is illustrated in FIGS. 13-15. Referring to FIG. 13, there is illustrated the face 180 of the distal end 14 of a typical endoscope 10. The face 180 includes two light source windows 182 for providing a light source to illuminate the area of observation, an optics window 184 and a biopsy/suction port 186. In the present invention, in which an endoscope sheath 36 will be used, the biopsy/suction port 186 within the endoscope 10 will not be used. However the light source 182 and the optics window 184 are used. When the sheath 36 is in place, as illustrated in FIG. 1, the face 180 is adjacent the window 48 of the endcap 40, as illustrated in phantom in FIGS. 4 and 6.

In order to reduce glare, the face 180 of the endoscope 10 is provided with a shadow mask 190, illustrated in FIG. 14. The shadow mask 190 is a light impeder designed to prevent glare by blocking light from the light sources 182 which may reflect off the window 48 of the endcap 40 and into the optics window 184. The shadow mask 190 may be made of paper, cloth, rubber, plastic or any other suitable material, and may be in the form of a decal or stencil adhesively placed on the face 180.

Figure 16:
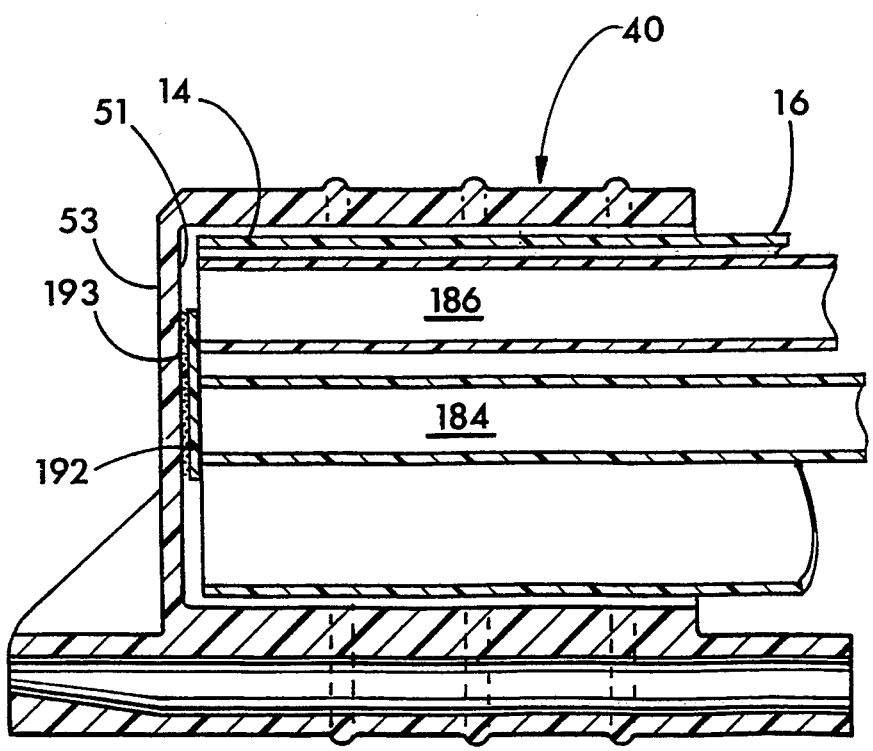
FIG. 16 is a side cross-sectional view of the endoscope cap taken along line 16—16 in the FIG. 15.

An alternative to the shadow mask 190 is illustrated in FIGS. 15 and 16, which show an endcap shadow mask 192 designed to be placed directly on the interior surface of the window 48 of the endcap 40. The endcap shadow mask 192 is designed to be positioned on the internal surface 51 of the window 48 by an adhesive 193 or the like in such a manner to block the glare from the light source 182 to the optics window 184. The endcap shadow mask 192 can be made of materials similar to that described with respect to the shadow mask 190. Additionally, it is within the scope of the present invention to create the endcap shadow mask 192 by using an anti-glare optical coating or by integrally associating the shadow mask directly to the internal surface 51 of the window 48 by frosting the shadow mask 192 portion of the window 48 or by building an elevated ridge on the window 48.

It is understood that the invention is not confined to the particular construction and arrangement herein illustrated and described, but embraces such modified forms thereof as come within the scope of the following claims.

What is claimed is:

1. A protective covering adapted for use on a conventional endoscope which includes an elongated substantially cylindrical portion having a distal end and a proximal end, wherein the distal end has substantially the same diameter as the cylindrical portion of the endoscope, the endoscope further including an optical element and a light source, the covering comprising:

(a) an elongated hollow sheath having a wall of flexible material, the material being substantially gas and water impervious, the sheath including a main channel adapted to contain the elongated portion of the endoscope in a loose fitting manner, a proximal end and a distal end, wherein the distal end of the sheath comprises an end-fitting cap having a first end, second end, a substantially cylindrical sidewall, forming an internal endoscope receiving chamber, wherein the chamber has a diameter slightly larger than the diameter of the distal end of the conventional endoscope such that the end-fitting cap is adapted to receive the distal end of the endoscope in a snug-fit relationship, and at least one access channel, the first end including an optically clear element having an external surface and internal surface, and wherein the second end of the cap is in sealing engagement with the distal end of the sheath; and (b) at least one axially-directed access tube, the access tube being adapted to extend alongside and exterior to the elongated substantially cylindrical portion of the endoscope, the access tube having a distal and a proximal end, wherein the access tube is separate from the sheath and adapted to be tangentially located on the elongated substantially cylindrical portion of the endoscope, wherein the access tube is adapted to extend axially between the elongated substantially cylindrical portion of the endoscope and the wall of the sheath, and wherein the main channel of the sheath has a sufficiently greater diameter, when unstretched, than the sidewall of the end-fitting cap to allow the access tube to move freely over the substantially cylindrical portion of the endoscope.

2. The covering of claim 1 wherein the optically clear element is concave.

3. The covering of claim 1 wherein the first end of the end-fitting cap comprises a utility opening for the access channel.

4. The covering of claim 1 wherein the access channel is provided with an instrument positioning ramp at the utility opening.

5. The covering of claim 1 wherein the distal end of the access channel is peripherally located on the first end of the cap and extends beyond the first end of the cap a sufficient distance to permit observation of the instrument exiting from the distal end of the access channel.

6. The covering of claim 1 wherein the at least one axially directed access channel extends in axial fashion along the sheath.

7. The covering of claim 1 comprising one access tube.

8. The covering of claim 1 comprising at least two access tubes.

9. The covering of claim 1 wherein the first end of the end-fitting cap comprises an extension with a utility opening.

10. The covering of claim 1 further comprising means to engage the proximal end of the sheath to the elongated portion of the endoscope.

11. The covering of claim 10 wherein the engagement means comprises an elastic constricting band to sealingly engage the proximal end of the sheath to the elongated portion of the endoscope.

12. The covering of claim 10 wherein the proximal end of the sheath is defined by a collar and the engagement means comprises a fastener attached to the endoscope, which fastener detachably engages the collar.

13. The covering of claim 12 wherein the collar is provided with a notch to accommodate the fastener.

14. The covering of claim 12 wherein the fastener is a hook.

15. The covering of claim 14 wherein the fastener is a spring-biased hook.

16. The covering of claim 1 wherein the access tube is a separate hollow tubular piece extending contiguously with the wall of the sheath.

17. The covering of claim 1 further comprising means to clean the optically clear element.

18. The covering of claim 17 wherein the means to clean the exterior side of the optically clear element comprises at least one axially directed access channel and an opening located at the distal end of the access channel, which end extends beyond the distal end of the sheath, the opening being configured to direct a spray of cleansing fluid in the direction of the optically clear element.

19. The covering of claim 1 wherein the distal end of the access channel in the endcap includes an opening for a surgical tool.

20. The covering of claim 1 wherein the endcap comprises means to reduce light source glare reflecting from the internal surface of the optically clear element to the optical element of the endoscope.

21. The covering of claim 20 wherein the means to reduce light source glare comprises a shadow mask.

22. The covering of claim 21 wherein the shadow mask is attached to the distal end of the elongated portion of the endoscope.

23. The covering of claim 21 wherein the shadow mask is attached to the internal surface of the optically clear element of the endcap.

24. The covering of claim 21 wherein the shadow mask is integrally associated with the internal surface of the optically clear element of the endcap.

25. A combination protective covering and valve system adapted for use on a conventional endoscope which includes an elongated substantially cylindrical portion having a distal end and a proximal end, an optical element and a light source, comprising:
(a) an elongated hollow sheath having a wall of flexible material, the material being substantially gas and water impervious, the sheath including a main channel adapted to contain the elongated portion of the endoscope in a loose fitting manner, a proximal end and a distal end, wherein the distal end of the sheath comprises an end-fitting cap having a first end, second end, a substantially cylindrical sidewall, forming an internal endoscope receiving chamber, wherein the chamber has a diameter slightly larger than the diameter of the distal end of the conventional endoscope such that the end-fitting cap is adapted to receive the distal end of the endoscope in a snug-fit relationship, and at least one access channel, the first end including an optically clear element having an external surface and internal surface, and wherein the second end of the cap is in sealing engagement with the distal end of the sheath;
(b) at least one axially-directed access tube, the access tube being adapted to extend alongside and exterior to the elongated substantially cylindrical portion of the endoscope, the access tube having a distal and a proximal end, wherein the access tube is separate from the sheath and adapted to be tangentially located on the elongated substantially cylindrical portion of the endoscope, wherein the access tube is adapted to extend axially between the elongated substantially cylindrical portion of the endoscope and the wall of the sheath, and wherein the main channel of the sheath has a sufficiently greater diameter, when unstretched, than the sidewall of the end-fitting cap to allow the access tube to move freely over the substantially cylindrical portion of the endoscope; and
(c) means to communicate a functional activity to the at least one access tube.

26. The system of claim 25 wherein the functional activity comprises a fluid.

27. The system of claim 26 wherein the fluid is air, water, or an irrigating fluid.

28. The system of claim 25 wherein the functional activity comprises a vacuum.

29. The system of claim 25 wherein the means to communicate a functional activity to the at least one access tube comprises a handle attachment adapted to be removably attached to the endoscope, the handle attachment comprising at least one actuator button, wherein the actuator button communicates with a valve system to supply the functional activity.

30. The system of claim 26 wherein the valve system comprises means to provide an air source, water source or suction source to the access tube.

31. The system of claim 29 wherein the actuator button is an electrically-controlled button adapted to supply the functional activity.

32. The system of claim 29 wherein the actuator button is a mechanically-controlled button adapted to supply the functional activity.

33. The system of claim 29 wherein the actuator button is a pneumatically controlled air pilot valve button adapted to supply the functional activity.

34. The system of claim 25 further comprising means to engage the proximal end of the sheath to the elongated portion of the endoscope.

35. The system of claim 34 wherein the engagement means comprises an elastic constricting band to sealingly engage the proximal end of the sheath to the elongated portion of the endoscope.

36. The system of claim 34 wherein the proximal end of the sheath is defined by a collar and the engagement means comprises a fastener attached to the endoscope, which fastener detachably engages the collar.

37. The system of claim 25 wherein the means to communicate a functional activity to the at least one access tube is disposable.

38. The system of claim 25 wherein the at least one axially-directed access tube is adapted to provide a passageway for a surgical tool.

39. In combination with a conventional endoscope, which includes an elongated substantially cylindrical portion having a distal end and a proximal end, wherein the distal end has substantially the same diameter as the cylindrical portion of the endoscope, the endoscope further including an optical element and a light source, a protective covering comprising:

(a) an elongated hollow sheath having a wall of flexible material, the material being substantially gas and water impervious, the sheath including a main channel covering the elongated portion of the endoscope in a loose fitting manner, a proximal end and a distal end, wherein the distal end of the sheath comprises an end-fitting cap having a first end, a second end, a substantially cylindrical side wall forming an endoscope receiving chamber, wherein the chamber has a diameter slightly larger than the diameter of the proximal end of the endoscope such that the end-fitting cap receives the distal end of the endoscope in a snug-fit relationship, and at least on access channel, wherein the first end of the end-fitting cap includes an optically clear element having an external surface and an internal surface, and wherein the second end of the cap is in sealing engagement with the distal end of the sheath; and (b) at least one axially directed access tube, the access tube extending alongside and exterior to the elongated substantially cylindrical portion of the endoscope, the access tube having a distal end and a proximal end, wherein the access tube is separate from the sheath and tangentially located on the elongated substantially cylindrical portion of the endoscope, wherein the access tube extends axially between the elongated substantially cylindrical portion of the endoscope and the wall of the sheath, and wherein the main channel of the sheath has a sufficiently greater diameter, when unstretched, than the side wall of the end-fitting cap to allow the access tube to move freely over the substantially cylindrical portion of the endoscope.

* * * * *